United States Patent
Boecklein et al.

(10) Patent No.: US 11,400,442 B2
(45) Date of Patent: Aug. 2, 2022

(54) PROCESS FOR PRODUCING A VPO CATALYST

(71) Applicant: Clariant International Ltd, Muttenz (CH)

(72) Inventors: Sebastian Boecklein, Heufeld (DE); Gerhard Mestl, Munich (DE); Gabriele Bindseil, Bruckmuehl (DE); Rene Hausmann, Bad Aibling (DE); Sarah Limbrunner, Bruckmuehl (DE); Anna Waldschuetz, Tuntenhausen (DE)

(73) Assignee: CLARIANT INTERNATIONAL LTD, Muttenz (CH)

( * ) Notice: Subject to any disclaimer, the term of this patent is extended or adjusted under 35 U.S.C. 154(b) by 177 days.

(21) Appl. No.: 16/744,257

(22) Filed: Jan. 16, 2020

(65) Prior Publication Data
US 2020/0222893 A1  Jul. 16, 2020

(30) Foreign Application Priority Data

Jan. 16, 2019 (DE) .......................... 102019100983.9

(51) Int. Cl.
*B01J 37/16* (2006.01)
*B01J 27/18* (2006.01)
(Continued)

(52) U.S. Cl.
CPC .............. *B01J 37/16* (2013.01); *B01J 27/18* (2013.01); *B01J 37/0236* (2013.01); *C07D 307/60* (2013.01)

(58) Field of Classification Search
CPC ........ B01J 37/16; B01J 37/0236; B01J 27/18; B01J 27/19; B01J 27/199; C07D 307/60
(Continued)

(56) References Cited

U.S. PATENT DOCUMENTS 4,018,709 A   4/1977  Barone
4,147,661 A   4/1979  Higgins
(Continued)

FOREIGN PATENT DOCUMENTS

CN   10 5413725   *  3/2016   ............ B01J 27/198
CN   109046413      12/2018
(Continued)

*Primary Examiner* — Patricia L. Hailey

(57) ABSTRACT

The disclosure relates to a process for producing a VPO catalyst containing molybdenum and a vanadyl pyrophosphate phase, which comprises the steps: a) provision of a reaction mixture comprising a V(V) compound, a P(V) compound, an Mo compound, a reducing agent and a solvent, b) reduction of the V(V) compound by means of the reducing agent at least in parts to give vanadyl hydrogenphosphate in order to obtain an intermediate suspension, c) filtration of the intermediate suspension from step b) in order to obtain an intermediate, d) drying of the intermediate at a temperature of not more than 350° C. in order to obtain a dried intermediate and e) activation of the dried intermediate at a temperature above 200° C., characterized in that not more than 0.2% by weight of water, based on the weight of the reaction mixture, is present in step a) and no water is withdrawn during the reduction in step b). The disclosure further relates to a VPO catalyst which is able to be produced by the process of the disclosure and also a catalyst containing the molybdenum-containing vanadium-phosphorus mixed oxide.

20 Claims, 2 Drawing Sheets

(51) Int. Cl.
  *B01J 37/02* (2006.01)
  *C07D 307/60* (2006.01)

(58) Field of Classification Search
  USPC .......................................... 502/209, 211, 312
  See application file for complete search history.

(56) References Cited

U.S. PATENT DOCUMENTS

| | | | |
|---|---|---|---|
| 4,361,501 A | 11/1982 | Blum | |
| 5,364,824 A * | 11/1994 | Andrews | B01J 27/198 |
| | | | 502/209 |
| 5,521,134 A * | 5/1996 | Bortinger | B01J 23/92 |
| | | | 502/209 |
| 5,885,919 A * | 3/1999 | Bortinger | C07C 51/215 |
| | | | 502/209 |
| 5,929,256 A | 7/1999 | Felthouse | |
| 5,945,368 A * | 8/1999 | Felthouse | C07C 51/42 |
| | | | 502/209 |
| 5,959,124 A * | 9/1999 | Hashiba | B01J 23/002 |
| | | | 549/259 |
| 6,858,561 B2 | 2/2005 | Bortinger | |
| 8,000,918 B2 | 8/2011 | Fjield | |
| 8,048,820 B2 | 11/2011 | Brandstadter et al. | |
| 9,931,618 B2 | 4/2018 | Cotter | |
| 2005/0222435 A1* | 10/2005 | Weiguny | B01J 37/08 |
| | | | 549/259 |
| 2010/0210858 A1* | 8/2010 | Shan | C07C 51/215 |
| | | | 549/259 |
| 2012/0149919 A1 | 6/2012 | Altwasser | |
| 2013/0217897 A1* | 8/2013 | Shan | B01J 37/16 |
| | | | 549/260 |

FOREIGN PATENT DOCUMENTS

| | | |
|---|---|---|
| WO | 0222257 | 3/2002 |
| WO | 2011124733 | 10/2011 |

\* cited by examiner

PROCESS FOR PRODUCING A VPO CATALYST

CROSS-REFERENCE TO RELATED APPLICATIONS

This application claims the benefit of priority of German Patent Application no. 10 2019 100 983.9, filed Jan. 19, 2019, which is hereby incorporated herein by reference in its entirety.

BACKGROUND OF THE DISCLOSURE

Field

This application relates to chemical processes, specifically, processes for making catalysts suitable for vanadium-phosphorus oxide catalysts.

Technical Background

Maleic anhydride is a chemical intermediate of great economic importance. It is used, for example, in the production of alkyd and polyester resins, either alone or in combination with other acids. In addition, it is also a versatile intermediate for chemical synthesis, for example for the synthesis of γ-butyrolactone, tetrahydrofuran and 1,4-butanediol, which are in turn used as solvents or can be processed further to give polymers, for example polytetrahydrofuran or polyvinylpyrrolidone.

The production of maleic anhydride is generally carried out by partial oxidation of butane in the gas phase by means of molecular oxygen or by means of a gas containing molecular oxygen in the presence of a vanadium-phosphorus oxide catalyst (VPO catalyst) containing vanadyl pyrophosphate (VPP). Vanadyl pyrophosphate in pure form comprises vanadium in a valency of +4 and is particularly suitable for the production of maleic anhydride from unbranched saturated or unsaturated hydrocarbons having at least four carbon atoms. Both fixed-bed reactors and fluidized-bed reactors are employed.

VPO catalysts have only a low intrinsic activity in the reaction of n-butane to give maleic anhydride. For this reason, a large amount of catalyst is necessary for a satisfactory conversion. In addition, VPO catalysts are among the most expensive base metal catalysts, mainly because of the high costs of the starting materials for them. Consequently, it is desirable to improve the performance (activity and selectivity) and lifetime of VPO catalysts. It is known from the prior art that the performance of VPO catalysts can be improved by addition of foreign elements to the VPO phase, for example by addition of molybdenum (Mo promoter or Mo doping).

U.S. Pat. No. 5,929,256 discloses the synthesis of an active molybdenum-modified vanadium-phosphorus catalyst for producing maleic anhydride. Here, a compound containing significant proportions of 5-valent vanadium is reacted with a 5-valent phosphorus-containing compound in an alcoholic medium which is suitable for reducing the vanadium to an oxidation state below 5. Here, molybdenum is incorporated into the reaction product, forming a solid, molybdenum-modified precursor composition. The alcohol is removed in order to obtain a dried solid molybdenum-modified precursor composition. Shaped bodies which contain the dried solid molybdenum-modified precursor compound are shaped. The dried and shaped molybdenum-modified precursor compositions are activated in order to convert them into the active catalyst.

DE 10 2014 004786 A1 relates to a catalyst which contains a vanadium-phosphorus oxide and an alkali metal and in which the proportion by weight of alkali metal in the vanadium-phosphorus oxide is in the range from 10 to 400 ppm, based on the total weight of the vanadium-phosphorus oxide, a process for the production thereof and also the use of the catalyst for the gas-phase oxidation of hydrocarbons, especially for the production of maleic anhydride.

DE 2611290 A1 relates to a vanadium-phosphorus-oxygen catalyst complex which is characterized in that it comprises vanadium, phosphorus and Me as active main components in an atomic ratio of from 1:0.90 to 1.3:0.005 to 0.4, where Me is U, W or a mixture of elements selected from the group consisting of Zn, Cr, U, W, Cd, Ni, B and Si. A process for producing maleic anhydride, characterized in that a feed composed of straight-chain C4-hydrocarbons in the vapour phase is contacted at elevated temperatures with oxygen and the vanadium-phosphorus-oxygen catalyst complex, is also disclosed.

SUMMARY OF THE DISCLOSURE

In one aspect, the disclosure relates to a process for producing a VPO catalyst containing molybdenum and a vanadyl pyrophosphate phase, the process including:
  a) providing a reaction mixture comprising a V(V) compound, a P(V) compound, an Mo compound, a reducing agent and a solvent,
  b) reducing the V(V) compound by means of the reducing agent at least in parts to give vanadyl hydrogenphosphate in order to obtain an intermediate suspension,
  c) filtering the intermediate suspension from step b) in order to obtain an intermediate,
  d) drying of the intermediate at a temperature of not more than 350° C. in order to obtain a dried intermediate and
  e) activating of the dried intermediate at a temperature above 200° C., wherein not more than 0.2% by weight of water, based on the weight of the reaction mixture, is present in step a) and no water is withdrawn during the reduction in step b).

In another aspect, the disclosure relates to a VPO catalyst that is able to be produced by the process of the invention and contains molybdenum and a vanadyl pyrophosphate phase.

In another aspect, the disclosure relates to methods for oxidizing butane to maleic anhydride using the catalysts of the disclosure.

Figure 1:
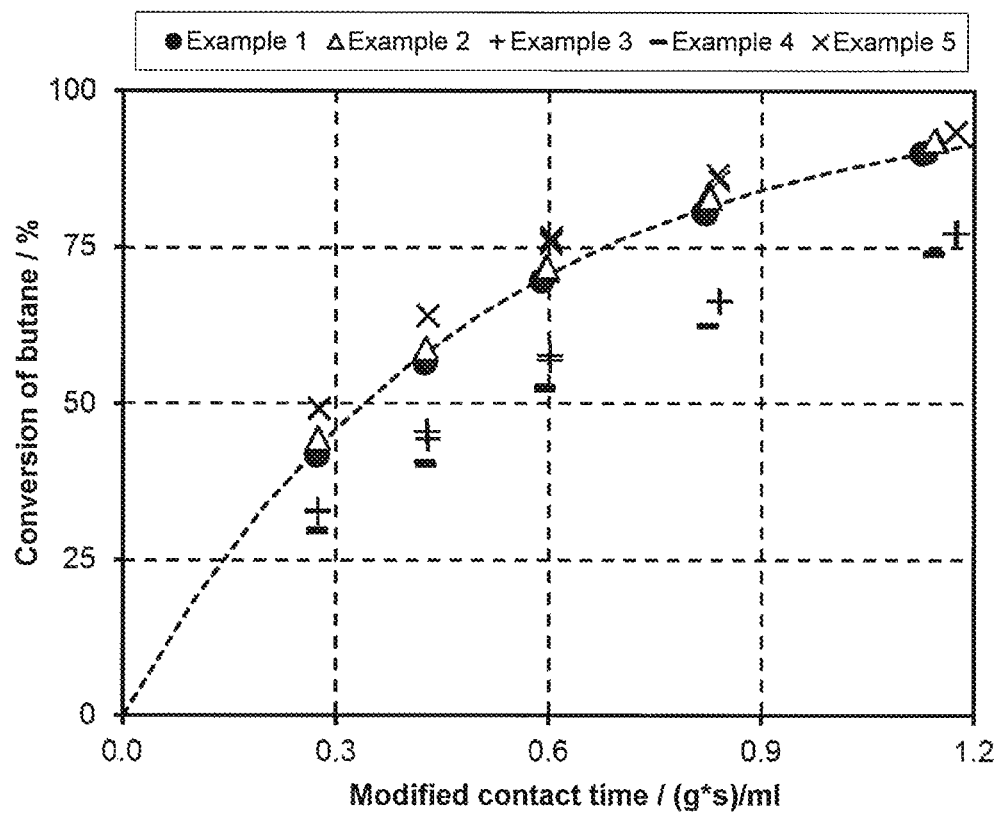
FIG. 1 is a plot of the conversion of butane as a function of the contact time for determining the catalyst activity in the Examples.

In one aspect, the disclosure relates to a process for producing a VPO catalyst containing molybdenum and a vanadyl pyrophosphate phase, the process including:

DETAILED DESCRIPTION

In order to produce VPO catalysts which contain a VPP phase, a reduction of vanadium pentoxide ($V_2O_5$) in the simultaneous presence of phosphoric acid (PPA) in an organic alcoholic solvent using benzyl alcohol as reducing agent is usually carried out, forming vanadyl hydrogenphosphate (VHP) together with benzaldehyde. The redox reaction which occurs (the "reduction"), in which vanadium in the oxidation state V (V(V)) reacts to form the VHP phase in which vanadyl species ($VO^{2+}$) is present with vanadium in the oxidation state IV (V(IV)), is:

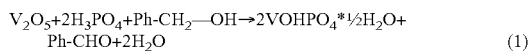

$$V_2O_5 + 2H_3PO_4 + Ph\text{-}CH_2\text{—OH} \rightarrow 2VOHPO_4 * \tfrac{1}{2}H_2O + Ph\text{-}CHO + 2H_2O \tag{1}$$

In a subsequent activation step, the VHP phase is converted under the action of heat with elimination of water into the vanadyl pyrophosphate phase.

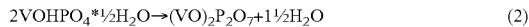

$$2VOHPO_4 * \tfrac{1}{2}H_2O \rightarrow (VO)_2P_2O_7 + 1\tfrac{1}{2}H_2O \tag{2}$$

As can be seen from reaction equation (1), two equivalents of water are liberated in the reduction step. Even when water-free solvent, usually isobutanol (IBA), and water-free reactants are used in this organic route for the VHP catalyst synthesis, the water formed during the reaction which proceeds leads to increasing dilution of the reaction mixture with water. It has hitherto been assumed that the presence of the water formed is disadvantageous and decreases the performance of the resulting catalyst. Accordingly, means of removing the resulting water, either physically, e.g. with the aid of a water separator, or chemically by the use of compounds which bind the water formed, i.e., for example, anhydrides such as phosphoric acid having a concentration of more than 100%, have hitherto been used during the reduction.

It has surprisingly been found that especially in the case of VPO catalysts comprising molybdenum and a vanadyl pyrophosphate phase, the presence of the water formed by the reduction is beneficial for the catalyst performance, in particular when no water is present at the beginning of the reduction. In particular, the effectiveness of the molybdenum promoter for reducing the by-products, mainly acetic acid (AcA) and acrylic acid (AcrA), is positively influenced.

Thus, the disclosure provides an improved VPO catalyst for the gas-phase oxidation of hydrocarbons, in particular for producing maleic anhydride by oxidation of butane. VPO catalysts of the disclosure can, for example, display improved catalyst performance, i.e., an improved activity and/or selectivity as a result of reduced by-product formation, and/or improved stability, and also processes for the production and use thereof.

One aspect of the disclosure is a process for producing a VPO catalyst containing molybdenum and a vanadyl pyrophosphate phase, which comprises the steps:
a) provision of a reaction mixture comprising a V(V) compound, a P(V) compound, an Mo compound, a reducing agent and a solvent,
b) reduction of the V(V) compound by means of the reducing agent at least in parts to give vanadyl hydrogenphosphate in order to obtain an intermediate suspension,
c) filtration of the intermediate suspension from step b) in order to obtain an intermediate,
d) drying of the intermediate at a temperature of not more than 350° C. in order to obtain a dried intermediate and
e) activation of the dried intermediate at a temperature above 200° C., wherein that not more than 0.2% by weight of water, based on the weight of the reaction mixture, is present in step a) and no water is withdrawn during the reduction in step b).

The V(V) compound that is used as starting material in the reaction mixture of step a) is a compound which contains vanadium in the oxidation state V and is preferably $V_2O_5$.

The P(V) compound that is used as starting material in the reaction mixture of step a) is a compound which contains phosphorus in the oxidation state V and is preferably phosphoric acid, or a phosphate salt such as $Na_3PO_4$. The phosphoric acid used ($H_3PO_4$) is preferably water-free (100 percent phosphoric acid) or phosphoric acid which contains only small amounts of water, i.e. phosphoric acid having a concentration of from 98 to 100%, preferably from 99 to 100% (the figure relates to the conventionally reported percentage proportion by weight of phosphoric acid based on the weight of the water/phosphoric acid mixture). As an alternative, it is possible to use phosphoric acid having a strength of more than 100%, which reacts with the water possibly present in the reaction mixture of step a) at the beginning to form phosphoric acid having a concentration of from 98 to 100%, preferably from 99 to 100%, more preferably 100%, so that no phosphoric acid having a concentration of more than 100% is present in the reaction mixture of step a) and at the same time not more than 0.2% by weight of water, based on the weight of the reaction mixture, remains in the reaction mixture.

The Mo compound that is used as starting material in the reaction mixture of step a) is any compound containing molybdenum, for example molybdenum trioxide, ammonium heptamolybdate (($NH_4)_6Mo_7O_{24}$)*$4H_2O$), ammonium paramolybdate (($NH_4)_6Mo_7O_2$*$4H_2O$), meta-molybdate, molybdic acid ($H_2MoO_4$) and also salts thereof such as ($NH_4)_2MoO_4$, $Na_2MoO_4$ or $K_2MoO_4$.

The reducing agent present in the reaction mixture of step a) can be any reducing agent that is able to reduce the V(V) compound so as to at least partly form vanadyl hydrogenphosphate. The reducing agent is preferably an aromatic alcohol, in particular benzyl alcohol, as an alternative ethanol or isobutanol.

The solvent present in the reaction mixture of step a) is preferably a high-boiling aliphatic alcohol, in particular isobutanol, as an alternative ethanol or isopropanol.

The reaction mixture of step a) preferably contains from 50 to 80% by weight of solvent, from 5 to 15% by weight of reducing agent, from 5 to 15% by weight of V(V) compound, from 5 to 15% by weight of the P (V) compound and from 0.05 to 0.3% by weight of the Mo compound, in each case based on the total weight of the mixture. The reaction mixture of step a) preferably contains from 60 to 70% by weight of isobutanol, from 5 to 15% by weight of benzyl alcohol, from 5 to 15% by weight of $V_2O_5$, from 10 to 20% by weight of phosphoric acid and from 0.1 to 0.2% by weight of a molybdate salt such as ammonium dimolybdate, in each case based on the total weight of the reaction mixture.

As described above, in certain aspects of the disclosure not more than 0.2% by weight of water, based on the weight of the reaction mixture, is present in the reaction mixture of step a), i.e. before the reduction step b). It may have to be ensured by means of suitable measures that not more than 0.2% by weight of water, based on the weight of the reaction mixture, is present; this can, for example, be effected by means of a water separator or chemically by the use of compounds which bind the water, for example, anhydrides such as phosphoric acid having a concentration of more than 100%. Preference is given to the reaction mixture of step a) comprising not more than 0.15% by weight of water, particularly preferably less than 0.10% by weight of water, even more preferably less than 0.05% by weight of water, most preferably less than 0.01% by weight of water, in each case based on the total weight of the reaction mixture. The reaction mixture of step a) can also contain from 0.05% by weight of water to 0.2% by weight of water, preferably from 0.1 to 0.15% by weight of water. The reaction mixture of step a) can also be water-free within the detection limit.

In process step b), the V(V) compound is at least partly reduced to an intermediate which contains molybdenum and a vanadyl hydrogenphosphate phase and together with the solvent and the other components from step a) forms the intermediate suspension. This reduction preferably occurs under reflux at atmospheric pressure, with the temperature being increased as a function of the boiling point of the solvent used, and preference is given to carrying out only a single reflux step in the process of the invention. The intermediate preferably contains vanadyl hydrogenphosphate as main phase or can even consist essentially of vanadyl hydrogenphosphate phase. The molybdenum which is likewise present in the intermediate can be present as dopant in the vanadyl hydrogenphosphate phase, with molybdenum doping meaning that the molybdenum is either incorporated into the vanadyl hydrogenphosphate phase or is present on the surface thereof. However, further vanadium-phosphorus mixed oxides in which vanadium has an oxidation state of IV or even III can also be formed in addition to the vanadyl hydrogenphosphate phase in the reduction. The reduction does not have to proceed to completion, so that proportions of the V(V) compound and the P(V) compound also remain in the intermediate and thus in the intermediate suspension. However, the intermediate formed in the reduction typically has an average oxidation state of vanadium of from 3.8 to 4.2.

As described above, in certain aspects of the disclosure, the water formed during the reduction should not be removed from the reaction mixture during the reduction, i.e. unlike the methods of the prior art, no agents which remove water are introduced at the point in time of the reduction. The removal of the water during the reduction is according to the prior art carried out either physically, e.g. with the aid of a water separator, or chemically by the use of compounds which bind the water, i.e., for example, anhydrides such as phosphoric acid having a concentration of more than 100%. Thus, the reaction mixture after step a) does not comprise any anhydrides which react with water and bind the latter; in particular, the reaction mixture after step a) does not comprise any phosphoric acid having a concentration of more than 100%.

Process step c), i.e. the filtration of the intermediate suspension, can be carried out by the means known to a person skilled in the art, typically using a filter press, a decanter or a suction filter.

The drying of the intermediate obtained by filtration (the solid residue from the filtration) in step d) can be carried out at a temperature above room temperature, typically at a temperature of up to 300° C., under reduced pressure or vacuum or under inert gas such as nitrogen or a noble gas. Drying preferably occurs in two steps $d_1$) drying under reduced pressure in the range from 90° C. to 140° C. and $d_2$) drying under nitrogen in the range from 230 to 300° C.

The drying step d) can optionally be followed by one or more of the process step(s):
$d_3$) mixing of from 1 to 10% by weight of graphite into the intermediate in order to obtain an intermediate mixture,
$d_4$) compaction and/or granulation of the intermediate or the intermediate mixture and
$d_5$) tableting of the intermediate or the intermediate mixture.

In process step e), the intermediate obtained is activated at a temperature above 200° C. Activation is typically carried out in a gas mixture consisting of air, nitrogen and water vapour at a temperature in the range from 300° C. to 500° C., preferably in the range from 350° C. to 450° C. The activation gives the finished catalyst as end product. If the graphite-containing intermediate mixture is activated, a graphite-containing catalyst is obtained as end product. The tableted end product typically has a lateral compressive strength of from 15 to 45 N.

The end product without graphite comprises vanadyl pyrophosphate with an excess of phosphate, so that a stoichiometry of $(VO)_2P_2O_7Mo_mP_2pO_y$, where m is in the range from 0.003 to 0.03, preferably from 0.006 to 0.02, particularly preferably from 0.012 to 0.019, p is in the range from 0 to 0.2 and y assumes a value required to achieve charge neutrality (at an average oxidation state of the vanadium of 4.0 and p=0, y is 0), is obtained.

EXAMPLES

A series of syntheses with variation of the proportions of water before and during the reflux step was carried out.

Example 1 is an example according to the disclosure in which the water concentration increases during the course of the reaction as a result of the water formed in the synthesis. Example 2 is intended to reproduce Example 1 using cheaper starting materials (105% PPA and 98.5% IBA), with it being assumed that the 105% PPA reacts with the water present in the IBA to form 100% PPA and pure IBA. Examples 3 and 4 are intended to demonstrate the influence of water at the beginning of the synthesis (about the same water concentration as after the completed reaction). In Example 5, the water concentration is kept constant during the entire reflux operation by use of a water separator.

Example 1 (According to the Disclosure)

Laboratory Synthesis of the End Product

A heating metal in which a 2 l four-neck flask is present is placed on a laboratory jack. A half-moon stirrer having a close-fitting stirring connection, which is connected by means of a stirrer coupling to the stirring mechanism, is present in the central opening of the four-neck flask. In the right-hand opening there is a thermometer, and in the left-hand opening there is a riser tube to the reflux condenser. The opening at the front in the middle is used for charging with the chemicals, and the nitrogen flushing is then connected there. The total apparatus can also be flooded with nitrogen. For this purpose, the nitrogen is firstly passed through a gas wash bottle and then introduced into the apparatus and discharged again from the top of the condenser through a gas wash bottle.

Production of the Reaction Mixture and Reduction 1069.5 g of isobutanol and 156.0 g of benzyl alcohol are firstly added. While stirring, 150 g of $V_2O_5$ are added. After the addition of $V_2O_5$, 2.52 g of ammonium dimolybdate are added. 232.50 g of phosphoric acid (100%, or water-free) are subsequently added to the suspension and the suspension is heated under reflux under $N_2$ for 10 hours.

Filtration

After cooling of the intermediate suspension, the suspension is transferred from the four-neck flask into a suction filter and the liquid is drawn off. The moist filter cake is pressed dry overnight in a press at from 14 to 18 bar.

Drying

The pressed filter cake is introduced into the evaporator flask of a rotary evaporator. The filter cake is dried overnight at 110° C. under a water pump vacuum. The powder which has been dried in this way is placed in a suitable calcination pot in a furnace and calcined at temperatures of from 200 to 300° C. in an $N_2$ atmosphere for 9 hours. The dried intermediate ($VMo_{0.0088}OHPO_4 \times 0.5\ H_2O$) is obtained.

Tableting

Before compaction/tableting, 5% by weight of graphite are added to the calcined pulverulent intermediate and the mixture is homogeneously mixed by means of a drum hoop mixer. This powder is compacted in a roller compactor at a contact pressure of 190 bar, a gap width of 0.60 mm and a roller speed of 7 rpm to give plates and granulated through a 1 mm sieve.

The granulated material is pressed by means of a rotary tableting press to give the desired pellet shape, with appropriate height, e.g. 5.6×5.6×2.3 mm, and lateral compressive strength.

Activation to Form the Pyrophosphate:

The activation in which vanadium pyrophosphate is formed is carried out under controlled conditions in a retort installed in a programmable furnace. The calcined pellets are introduced uniformly into the retort and the latter is closed tightly. The catalyst is then activated in a humid air/nitrogen mixture (50% absolute atmospheric humidity) firstly at above 300° C. for 5 hours and subsequently at above 400° C. for 9 hours.

Example 2 (According to the Disclosure)

The synthesis was carried out as in Example 1, but 105% strength phosphoric acid (PPA) was used instead of 100% PPA and, furthermore, isobutanol containing 1% by weight of distilled water was used instead of water-free isobutanol (according to the weights used, pure isobutanol and 100% PPA are formally obtained again).

Example 3 (Comparison)

The synthesis was carried out as in Example 1, but the high-purity isobutanol was admixed with 2% by weight, based on the weight of the isobutanol, of distilled water.

Example 4 (Comparison)

The synthesis was carried out as in Example 1, but the high-purity isobutanol was admixed with 5% by weight, based on the weight of the isobutanol, of distilled water.

Example 5 (Comparison)

The synthesis was carried out as in Example 1, but a water separator was integrated into the reflux apparatus so as to withdraw water during the reflux step of the reaction.

Catalyst Performance

Figure 2:
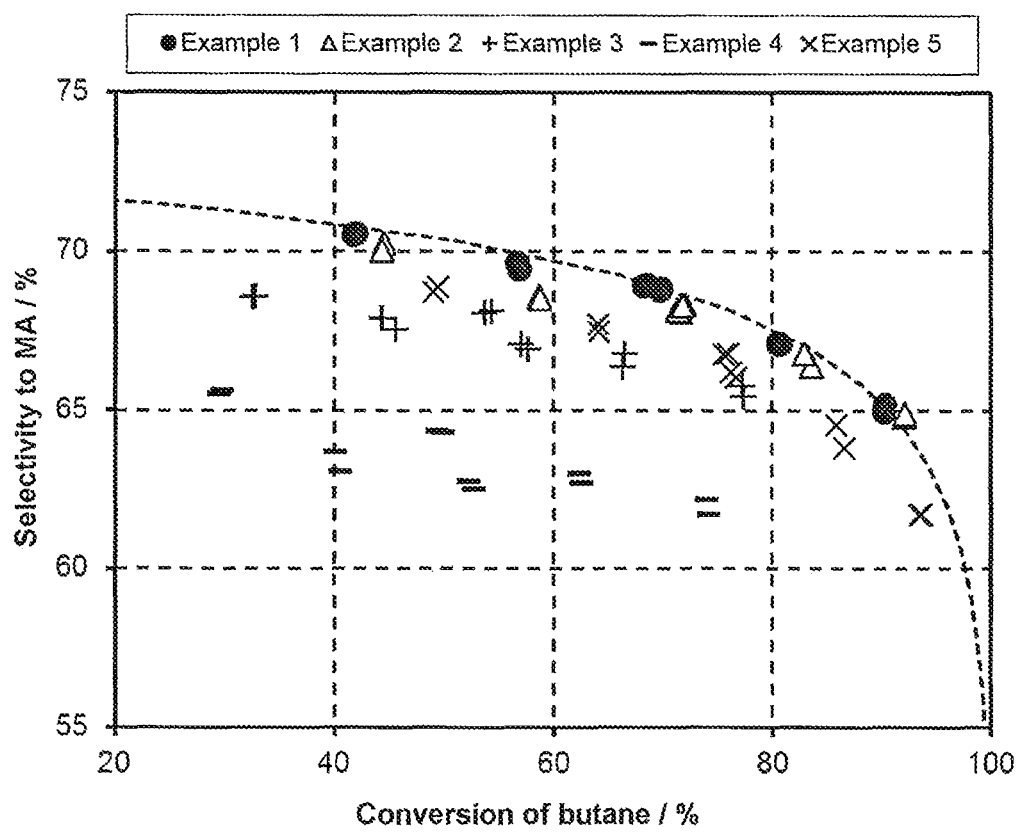
FIG. 2 is plot of the conversion of butane versus the selectivity to maleic anhydride in the Examples.

To determine the catalyst performance, all catalysts were, after the preparation had been completed (reflux, filtration, vacuum drying, calcination, compacting, tabletting, activation), tested in respect of their catalytic properties in a "bench scale" reactor using 1.5 mol % of butane in air in a diluted catalyst bed (1:9 mixture of catalyst:inert ceramic rings). To determine the catalyst activity, the reaction rate constant $k_a$ was determined at a reaction temperature of 410° C. by plotting the conversion of butane against the modified residence time (ratio of catalyst mass and inflow volume stream—the otherwise customary contact time cannot be used since measurements are carried out in a diluted catalyst bed) assuming $1^{st}$ order kinetics. FIG. 1 shows the experimental data, and also a fitting to Example 1 assuming $1^{st}$ order kinetics (broken line curve). The selectivity to maleic anhydride (MA) was determined for the industrially relevant reference conversion of 85% from the experimental data by plotting the selectivity against the conversion of butane (FIG. 2). An analogous procedure was also carried out for the by-products acetic acid and acrylic acid. The results of the evaluation of the catalyst performance are described in Table 1.

TABLE 1

Summary of the test results in respect of activity ($k_a$) and selectivity to MA, AcA and AcrA at 85% conversion of butane.

| Example | Reflux conditions | $k_a$ [mL/(g*s)] | $S_{MA}$ @ 85% X | $S_{AcA}$ @ 85% X | $S_{AcrA}$ @ 85% X |
|---|---|---|---|---|---|
| 1 | <0.2% of water* | 2.0 | 66.5 | 0.18 | 0.17 |
| 2 | <0.2% of water* | 2.1 | 66.5 | 0.22 | 0.28 |
| 3 | +2% of water* | 1.3 | 64.3 | 0.20 | 0.14 |
| 4 | +5% of water* | 1.2 | 59.8 | 0.18 | 0.14 |
| 5 | Water separator | 2.4 | 64.7 | 0.20 | 0.17 |

*% by weight of water based on the weight of the reaction mixture before the reduction.

What is claimed is:

1. A process for producing a VPO catalyst containing molybdenum and a vanadyl pyrophosphate phase, the process comprising:
    a) providing a reaction mixture comprising a V(V) compound, a P(V) compound, an Mo compound, a reducing agent and a solvent, the reaction mixture not comprising any compound that reacts with or binds with water,
    b) reduction of the V(V) compound by means of the reducing agent at least in part to give vanadyl hydrogenphosphate and water in order to obtain an intermediate suspension,
    c) filtration of the intermediate suspension from step b) in order to obtain an intermediate,
    d) drying of the intermediate at a temperature of not more than 350° C. in order to obtain a dried intermediate and
    e) optionally, activating the dried intermediate at a temperature above 200° C.,
wherein that not more than 0.2% by weight of water, based on the weight of the reaction mixture, is present in step a) and no water is removed during the reduction in step b).

2. The process according to claim 1, wherein the V(V) compound is $V_2O_5$.

3. The process according to claim 1, wherein the reaction mixture of step a) does not comprise any phosphoric acid having a concentration of more than 100%.

4. The process according to claim 1, wherein the P(V) compound is phosphoric acid having a concentration in the range from 98 to 100%.

5. The process according to claim 1, wherein the reducing agent is an aromatic alcohol.

6. The process according to claim 1, wherein the solvent is an aliphatic alcohol.

7. The process according to claim 1, wherein the reduction is carried out under reflux at atmospheric pressure.

8. The process according to claim 1, wherein the drying is carried out under reduced pressure.

9. The process according to claim 1, further comprising mixing of the dried intermediate from step d) with from 2 to 10% by weight of graphite, based on the total weight of the mixture, and granulation of the mixture in order to obtain a granular material.

10. The process according to claim 1, further comprising tabletting of the dried intermediate to obtain pellets.

11. The process according to claim 1 wherein activating step (e) is performed.

12. The process according to claim 11 wherein the activating step (e) is performed at a temperature above 200° C. in a gas mixture containing nitrogen.

13. The process according to claim 1, wherein not more than 0.15% by weight of water is present based on the total weight of the reaction mixture, is present in step (a).

14. The process according to claim 1, wherein from 0.01 to 0.1% by weight of water is present in step (a).

15. The process according to claim 1, wherein
the P(V) compound is phosphoric acid having a concentration in the range from 98 to 100%;
the V(V) compound is $V_2O_5$;
the reducing agent is an aromatic alcohol; and
the solvent is an aliphatic alcohol.

16. The process according to claim 15, wherein
the reduction is carried out under reflux at atmospheric pressure,
the drying is carried out under reduced pressure.

17. The process according to claim 16, wherein activating step (e) is performed.

18. A VPO catalyst made by a process according to claim 1.

19. A method for oxidizing butane to maleic anhydride comprising contacting the VPO catalyst of claim 18 with butane and oxygen.

20. The process according to claim 1, wherein the reaction mixture of step (a) is formed by a process comprising combining a phosphoric acid having a concentration in excess of 100% with a water-containing solvent, such that the phosphoric acid reacts with the water to provide a phosphoric acid concentration no more than 100%.

* * * * *